United States Patent
Ahn (10) Patent No.: US 9,826,990 B2
(45) Date of Patent: Nov. 28, 2017

(54) REAMER FOR IMPLANT SURGERY

(71) Applicant: Sang-Hoon Ahn, Daejeon (KR)

(72) Inventor: Sang-Hoon Ahn, Daejeon (KR)

( * ) Notice: Subject to any disclaimer, the term of this patent is extended or adjusted under 35 U.S.C. 154(b) by 404 days.

(21) Appl. No.: 14/372,201

(22) PCT Filed: Feb. 14, 2013

(86) PCT No.: PCT/KR2013/001137
§ 371 (c)(1),
(2) Date: Jul. 14, 2014

(87) PCT Pub. No.: WO2013/129790
PCT Pub. Date: Sep. 6, 2013

(65) Prior Publication Data
US 2015/0094725 A1    Apr. 2, 2015

(30) Foreign Application Priority Data

Mar. 2, 2012    (KR) .................. 10-2012-0021568

(51) Int. Cl.
*A61B 17/00*    (2006.01)
*A61B 17/16*    (2006.01)
*A61C 8/00*    (2006.01)
*A61C 3/02*    (2006.01)

(52) U.S. Cl.
CPC ...... *A61B 17/1688* (2013.01); *A61B 17/1615* (2013.01); *A61B 17/1673* (2013.01); *A61C 3/02* (2013.01); *A61C 8/0089* (2013.01); *A61C 8/0092* (2013.01)

(58) Field of Classification Search
CPC .................. A61B 17/1615; A61B 17/1617
USPC ......................... 408/211, 223, 224
See application file for complete search history.

(56) References Cited

U.S. PATENT DOCUMENTS 4,411,563 A * 10/1983 Moon ................. B23B 51/02
407/54

FOREIGN PATENT DOCUMENTS

| KR | 10-0792649 B1 | 1/2008 |
| KR | 10-2009-0056395 A | 6/2009 |
| KR | 10-1013285 B1 | 2/2011 |
| KR | 10-2011-0039880 A | 4/2011 |
| WO | WO 2009008606 A2 * | 1/2009 ......... A61B 17/1688 |

* cited by examiner

*Primary Examiner* — Si Ming Ku
(74) *Attorney, Agent, or Firm* — John K. Park; Park Law Firm (57) ABSTRACT

Disclosed is a reamer for implant surgery including: cutting front end portions each of which has a sharp front end; cut edges of a horizontal line form, the cutting front end portions and the cut edges being arranged radially and alternately, wherein one side of the cutting front end portion having the sharp front end has a triangular depressed face inclined downwardly toward a rotation central axis of the cutting part, and one side of the cut edge having the horizontal line form has a triangular inclined face inclined downwardly toward the outer circumferential surface of the cutting part, wherein an inclination angle of a side inclined edge inclined downwardly at the sides of the outer circumferences of the cutting front end portion and the cut edge becomes gradually smaller in the rotation direction of the cutting part.

1 Claim, 5 Drawing Sheets

-- Prior Art --

REAMER FOR IMPLANT SURGERY

TECHNICAL FIELD

The present invention relates to a reamer for forming a hole in a bone in order to plant an implant, and more particularly, to a reamer for implant surgery which can easily select a good position for a stable hole processing, can be rotated at high speed by increasing the bone cutting efficiency, and can reduce friction resistance even during the high speed rotation so as to increase workability for planting an implant.

BACKGROUND ART

Figure 1:
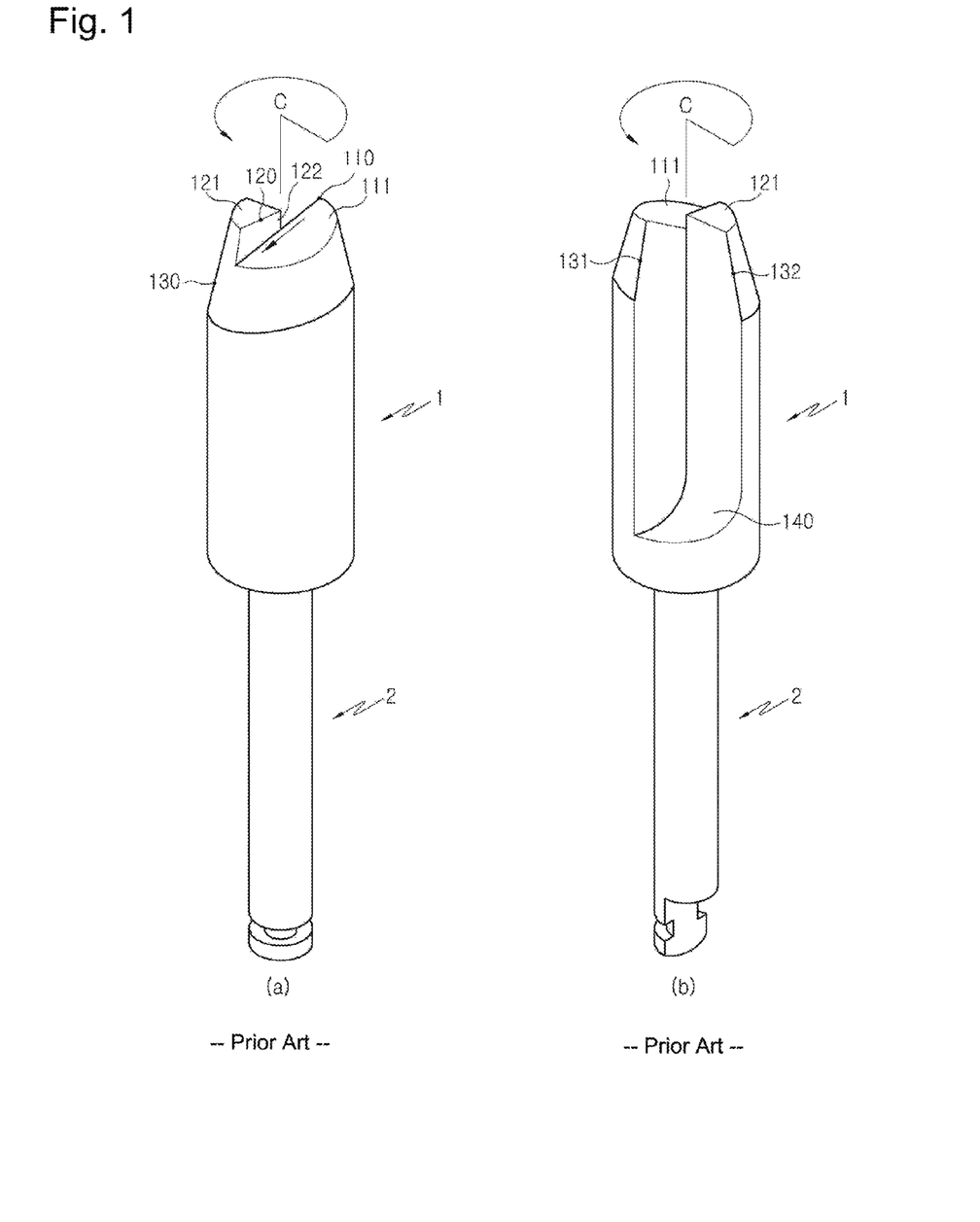
FIG. 1 is a perspective view of a reamer for implant surgery according to a conventional invention.
Figure 2:
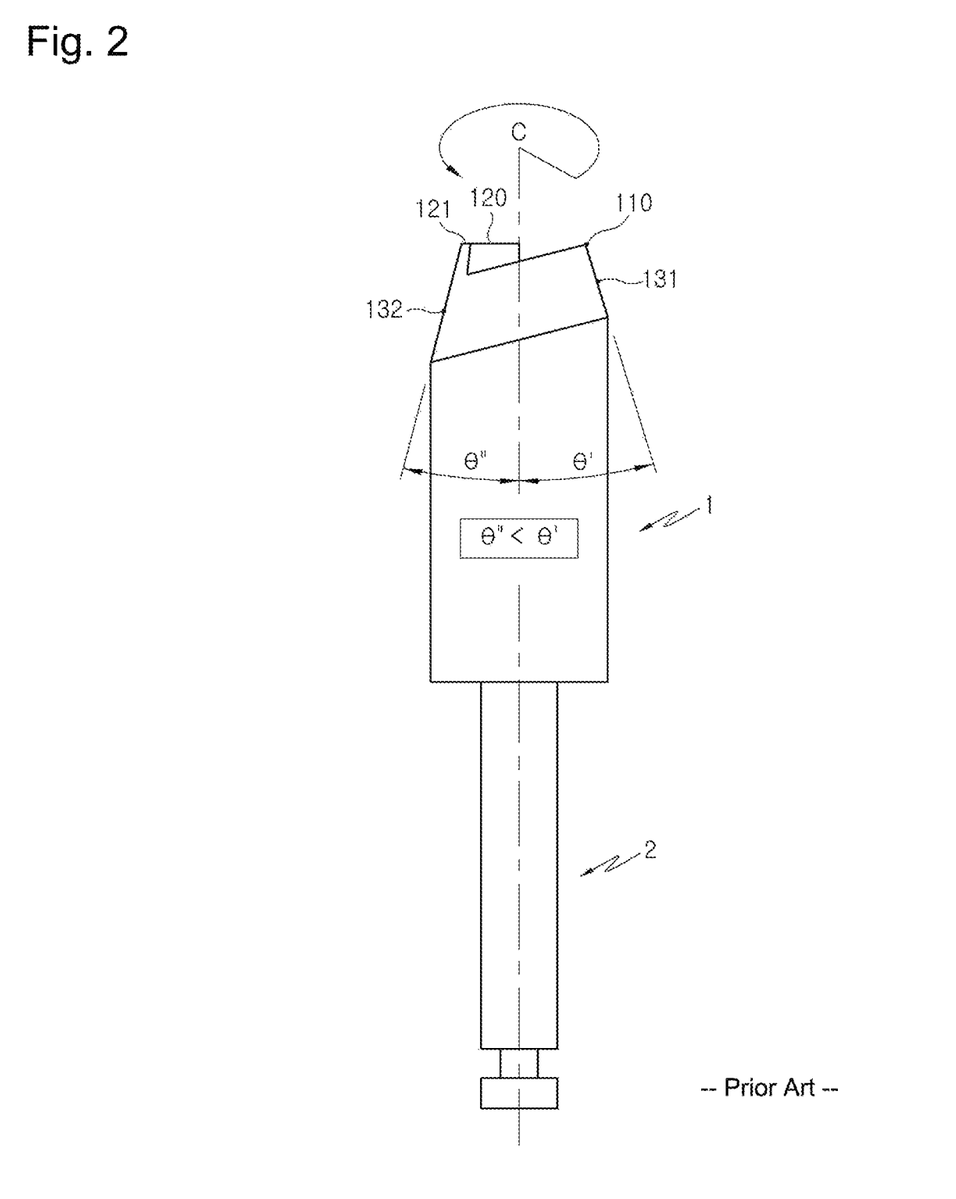
FIG. 2 is a front view of the reamer for implant surgery according to the conventional invention.

FIG. 1 is a perspective view of a reamer for implant surgery according to a conventional invention, and FIG. 2 is a front view of the reamer for implant surgery according to the conventional invention. As shown in FIGS. 1 and 2, the reamer for implant surgery according to the conventional invention includes: a protruding face 121 formed in such a manner as to upwardly upheave a partial surface including an outer circumference of a cutting part 1 out of the entire top surface of the cutting part 1 to form a stepped jaw 122; a depressed face 111 formed in such a manner as to depress a partial surface out of the entire top surface of the cutting part 1 according to the formation of the protruding face 121, on the contrary to the protruding face 121; a cut edge 120 formed on a connected portion between the stepped jaw 122 and the protruding face 121; and a discharge path 140 formed between the side surfaces of the depressed face 111 and the protruding face 121, wherein the depressed face 111 is upwardly slanted as it goes toward the front side of the stepped jaw 122 and becomes narrowed in width as it goes toward the end of the upper portion thereof so as to form a cutting front end portion 110 at the upper end thereof.

Moreover, the depressed face 111 and the protruding face 121 of the cutting part 1 form a tapered portion 130 along the outer peripheries thereof so as to form an initial inclined edge 131 at the boundary portion between the discharge path 140 and the outer periphery of the depressed face 111 and so as to form a final inclined edge 132 at the boundary portion between the discharge path 140 and the outer periphery of the protruding face 121, wherein the tapered portion 130 is decreased in an angle (θ) with respect to the axis of the reamer and is increased in width of the tapered portion 130 as it is rotated from the initial inclined edge 18 toward the final inclined edge 19.

The above-mentioned reamer for implant surgery according to the conventional invention is disclosed in Korean Patent No. 10-0792649 which was filed to the Korean Intellectual Property Office by the same inventor as the present invention.

However, the reamer for implant surgery according to the conventional invention has five disadvantages. First, as shown in FIG. 1, because the reamer for implant surgery according to the conventional invention includes the cutting front end portion 110 of which front end is sharp and which is eccentric based on a rotation central axis (C), it is difficult to carry out a centrum rotation on the rotation central axis (C) when the cutting part 1 is rotated.

That is, when rotary power is applied to the cutting part 1, power to rotate around the cutting front end portion 110 of which front end is sharp is generated, and hence, it is difficult to carry out the centrum rotation because there occurs a rotation interference relative to the rotation central axis (C) of the cutting part 1 which became the standard.

Therefore, when a user works using the conventional reamer for implant surgery as shown in FIG. 1, it must be rotated at low speed, and the rotation center must be first formed before the user uses the reamer in order to secure the centrum rotation of the cutting part 1.

Second, the conventional reamer is very low in cutting efficiency because it has one cutting front end portion 110, one cut edge 120 and one initial inclined edge 131. Third, the conventional reamer is low in cutting efficiency, there is a high probability of generating friction heat during the high speed rotation of the reamer because a contact area between the reamer and the bone is wide, and the reamer cannot carry out high speed rotation because there is a risk of bone heat necrosis by friction heat.

Fourth, because a passage through which physiological saline which can cool friction heat between the reamer and the bone during the rotation of the reamer can arrive at the cutting part is small, it is difficult to make the physiological saline arrive at the cutting part. Fifth, the conventional reamer must stop operation and frequently remove splinters of the bone in order to keep the cutting efficiency of the cutting part because a mooring space of the splinters of the bone generated by rotation of the reamer is small and it is difficult to discharge the splinters of the bone by rotation.

In the meantime, "AHN, Sang-Hoon" who is the applicant and the inventor of the present invention has done a lot of efforts to solve problems of the conventional reamer for implant surgery and to improve performance of the reamer, and as a result, and has contributed to industrial development by inventing a "reamer for implant surgery" disclosed in Korean Patent No. 10-0630304 and a "reamer for operating implant maxillary sinus" disclosed in Korean Patent No. 10-0792649.

SUMMARY

Technical Problem

Accordingly, the present invention has been made in an effort to solve the above-mentioned problems occurring in the prior arts, and it is an object of the present invention to provide a reamer for implant surgery which can obtain advanced actions and effects by using and improving some of the technical parts of the "reamer for operating implant maxillary sinus" disclosed in Korean Patent No. 10-0792649 issued to "AHN, Sang-Hoon" who is the applicant and the inventor of the present invention and by adding new parts to the reamer for operating implant maxillary sinus.

That is, in order to form a hole in the bone to plant an implant, first, the cutting front end portions 10 each of which has a sharp front end are formed symmetrically so as to provide a stable centrum rotation, and hence, the reamer can cut the bone into a round shape the two symmetrically formed cutting front end portions 10 are rotated to the centrum two times faster than the conventional reamer. Second, the reamer gets in line contact with the bone by inclinedly forming the flat cut edge 20 in order to cut the inner face in a round shape so as to reduce a contact area and remarkably increase cutting efficiency of the rounded inner face. Third, the reamer can cut the side four times faster than the conventional reamer because it has four initial inclined edges 131 by improving the structure that the conventional reamer has just one initial inclined edge.

Therefore, the reamer for implant surgery according to an embodiment of the present invention can secure the center of centrum rotation, reduce the contact area between the reamer and the bone to thereby remarkably increase cutting efficiency, and considerably increase cutting performance and workability through the high speed rotation.

Furthermore, it is another object of the present invention to provide a reamer for implant surgery which has a bone storage groove 31 formed between the cutting front end portion 10 and the cut edge 20 in order to naturally move autogenous bone crushed during hole processing to the maxillary sinus the moment a bone plate of the hole is opened without being discharged downward from the bone, such that the autogenous bone is pressed while being accumulated during rotation of the reamer.

Technical Solution

To achieve the above objects, the present invention provides a reamer for implant surgery including: cutting front end portions which are formed at the upper portion of a cutting part and each of which has a sharp front end; cut edges of a horizontal line form, the cutting front end portions and the cut edges being arranged radially and alternately, wherein one side of the cutting front end portion having the sharp front end has a triangular depressed face inclined downwardly toward a rotation central axis of the cutting part, and one side of the cut edge having the horizontal line form has a triangular inclined face inclined downwardly toward the outer circumferential surface of the cutting part, wherein a bone storage groove in which the residue of a bone being cut is inserted and accumulated is formed between the cutting front end portions and the cut edges which are arranged alternately, and wherein an inclination angle of a side inclined edge formed at the sides of the outer circumferences of the cutting front end portion and the cut edge becomes gradually smaller in the rotation direction of the cutting part.

Advantageous Effects

As described above, because the reamer for implant surgery according to the preferred embodiment of the present invention includes: two cutting front end portions 10 having sharp front ends and cut edges 20 of the horizontal line form to get in line contact with the bone 40, which are formed radially and alternately based on the rotation central axis (C) of the cutting part, the reamer can stabilize centrum rotation and enhance cutting efficiency by the cutting front end portions 10 formed symmetrically based on the rotation central axis (C) of the cutting part 1 so as to make high speed rotation possible, thereby increasing cutting power and working speed and keeping a stable cutting position due to the sharp cutting front end portions 10 which are formed symmetrically even when the reamer comes into contact with the bone 40.

Moreover, when the upper portion of the cutting part 1 is rotated in a state where it gets in contact with the bone 40, because the reamer comes into line contact with the bone 40 by the cut edges 20 of the horizontal line form each of which has the inclined face 21 inclined downward toward the rear side, the friction resistance with the bone 40 is reduced, and hence, the reamer according to the preferred embodiment of the present invention can increase cutting power and enhance working speed.

Furthermore, because the reamer includes the bone storage groove 31 formed between the cutting front end portion 10 and the cut edge 20, the residue of the eliminated bone 40 is naturally inserted and accumulated into the bone storage groove 31, such that the residue of the bone 40 does not hinder rotation of the cutting part 1, for instance, increase friction resistance, and the autogenous bone 43 accumulated in the bone storage groove 31 the moment the bone 40 is perforated pushes up the bone plate opened by the structure of the reamer while being inserted into the maxillary sinus 50 so as to prevent a damage of the sinus membrane 51 and to be utilized as a filling material necessary for fixing the implant core 60.

DETAILED DESCRIPTION OF INVENTION

Hereinafter, reference will be now made in detail to the preferred embodiment of the present invention with reference to the attached drawings.

The reamer for implant surgery according to a preferred embodiment of the present invention can obtain advanced actions and effects by using and improving some of the technical parts of the "reamer for operating implant maxillary sinus" disclosed in Korean Patent No. 10-0792649 issued to "AHN, Sang-Hoon" who is the applicant and the inventor of the present invention and by adding new parts to the reamer for operating implant maxillary sinus. In consideration of the above, the reamer for implant surgery according to the present invention will be described in comparison with the "reamer for operating implant maxillary sinus" disclosed in Korean Patent No. 10-0792649 shown in FIGS. 1 and 2.

FIGS. 1 and 2 are a perspective view and a front view of a reamer for implant surgery according to a conventional invention disclosed in Korean Patent No. 10-0792649. As shown in FIGS. 1 and 2, the conventional reamer for implant surgery in a maxillary sinus includes: a protruding face 121 formed in such a manner as to upwardly upheave a partial surface including an outer circumference of a cutting part 1 out of the entire top surface of the cutting part 1 to form a stepped jaw 122; a depressed face 111 formed in such a manner as to depress a partial surface out of the entire top surface of the cutting part 1 according to the formation of the protruding face 121, on the contrary to the protruding face 121; a cut edge 120 formed on a connected portion between the stepped jaw 122 and the protruding face 121; and a discharge path 140 formed between the side surfaces of the depressed face 111 and the protruding face 121, wherein the depressed face 111 is upwardly slanted as it goes toward the front side of the stepped jaw 122 and becomes narrowed in width as it goes toward the end of the upper portion thereof so as to form a cutting front end portion 110 at the upper end thereof.

However, as shown in FIG. 1, in the conventional reamer for implant surgery, the cutting front end portion 110 of which front end is sharp is formed eccentrically based on the rotation central axis (C). When rotary power is applied to the cutting part 1 by means of the connection part 2, because the rotary power of the cutting part 1 tries to carry out centrum rotation based on the rotation central axis (C) and there is rotary power which tries to rotate eccentrically based on the sharp cutting front end portion 110 at the same time with the centrum rotation of the cutting part 1, there is interference between the centrum rotation and the eccentric rotation, and hence, it is difficult to rotate at a stable position, and a user has to secure safety in hole processing while rotating the reamer at low speed not to generate friction heat between the reamer and the bone because the reamer is low in cutting efficiency. As described above, the low speed rotation of the cutting part 1 caused by eccentricity of the cutting front end portion 110 deteriorates cutting performance, extends the working period, and does not secure safety in hole processing.

Figure 3:
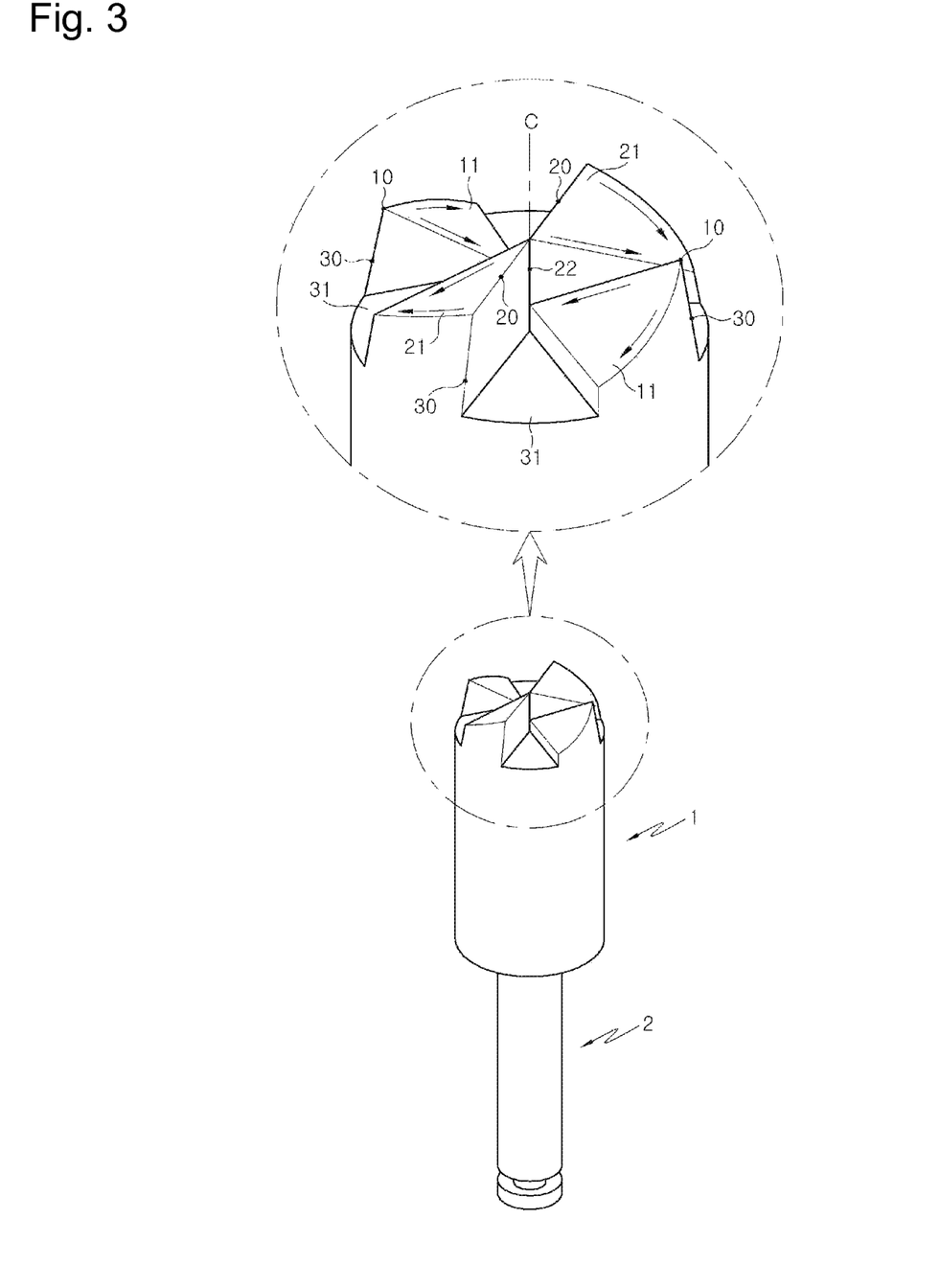
FIG. 3 is a perspective view of a reamer for implant surgery according to a preferred embodiment of the present invention.

FIG. 3 is a perspective view of a reamer for implant surgery according to a preferred embodiment of the present invention. As shown in the enlarged view of FIG. 3, in order to solve the problem caused by eccentricity of the cutting front end portion 110 which is one of the problems of the conventional reamer for implant surgery, the reamer for implant surgery according to the preferred embodiment of the present invention includes cutting front end portions 10 of each of which front end is sharp and which are formed symmetrically so as to carry out centrum rotation at a stable position at high speed while a hole is formed in a bone (40) to plant an implant.

That is, the cutting front end portions 10 having sharp front ends and cut edges 20 are formed radially and alternately, and in this instance, the two cutting front end portions 10 are formed symmetrically with each other, such that rotation of the cutting part 1 which carries out centrum rotation on a rotation central axis (C) and rotation of the two cutting front end portions 10 which are radially spaced at the same distance from the rotation central axis (C) form the same trace, such that there is no interference on rotation.

Therefore, the user can carry out hole processing stably through high speed rotation using the reamer according to the present invention because rotary power transferred to the cutting part 1 is not interfered by the cutting front end portions 10. Moreover, the reamer can stably get in contact with the bone 40 due to the two cutting front end portions 10 which are symmetric.

As shown in the enlarged view of FIG. 3, it is preferable that the cutting front end portions 10 which are sharpened come into point contact with the bone 40 when getting in contact with the bone 40 for hole processing so as to enhance initial cutting performance. As shown by an arrow in FIG. 3, each of the cutting front end portions 10 has a depressed face 11 disposed at the rear side thereof and downwardly inclined toward the center.

Meanwhile, the reamer for implant surgery disclosed in Korean Patent No. 10-0792649 shown in FIGS. 1 and 2 includes: the protruding face 121 formed in such a manner as to upwardly upheave the partial surface including an outer circumference of the cutting part 1 out of the entire top surface of the cutting part 1 to form the stepped jaw 122; and the cut edge 120 formed on the connected portion between the stepped jaw 122 and the protruding face 121. While the reamer forms a hole in the bone 40, the cutting front end portion 110 cuts the outer circumference of the hole in a round shape and the cut edge 120 cuts the bone 40 of the inside so as to carry out double cutting.

However, as shown in FIG. 1, the cut edge 120 of the conventional reamer is formed at the connection point between the stepped jaw 122 and the protruding face 121, and the flat protruding face 121 gets in surface contact with the bone 40 while the hole is formed in the bone 40. Such a surface contact between the protruding face 121 and the bone 40 may cause increase of friction resistance when the cut edge 120 shows cutting performance, and hence, cutting performance of the cut edge 120 according to the high speed rotation of the cutting part 1 is deteriorated.

Therefore, in order to solve the problem that the high speed rotation transferred to the cutting part 1 is deteriorated by friction resistance generated from the conventional flat protruding face 121, as shown in the enlarged view of FIG. 3, two cut edges 20 which are formed radially and alternately with the cutting front end portions 10 are formed symmetrically to each other. The cut edges 20 includes: a stepped jaw 22 formed at a portion where the cut edge 20 meets the depressed face 11 at the center of the cutting part 1; and an inclined face 21 formed at the rear side of the cut edge 20 and inclined downward toward the outer circumferential surface of the cutting part 1 as indicated by an arrow of FIG. 3, and finally, the cut edge 20 becomes a horizontal line form, and hence, comes into line contact with the bone 40.

Therefore, in the preferred embodiment of the present invention, the cut edge 20 gets not in surface contact with the bone 40 but in line contact with the bone 40, and hence, because the high speed rotation transferred to the cutting part 1 is used to hole processing as it is without any friction resistance caused by the surface contact, the reamer according to the preferred embodiment of the present invention can enhance cutting power of the cut edge 20 and reduce the work period. Additionally, as shown in the enlarged view of FIG. 3, because the two cut edge 20 of the horizontal line form are formed radially and alternately with the cutting front end portions 10, the reamer according to the preferred embodiment of the present invention doubles cutting power compared with the conventional reamer having just one cut edge 120.

In the meantime, the conventional reamer for implant surgery disclosed in Korean Patent No. 10-0792649 shown in FIGS. 1 and 2 includes the discharge path 140 formed between the side surfaces of the depressed face 111 and the protruding face 121 in order to smoothly discharge the residue of the cut bone 40, thereby enhancing friction resistance by the residue of the bone 40 not to deteriorate rotary power of the cutting part 1.

In addition, as shown in FIGS. 1 and 2, because the angle (θ') with respect to the rotation central axis (C) of the reamer becomes gradually smaller as the tapered portion 130 goes from the initial inclined edge 131 of the outer circumference of the depressed face 111 toward the final inclined edge 132 of the outer circumference of the protruding face 121, friction resistance generated when the reamer gets in contact with the bone 40 is maximized at the initial inclined edge 131 where the angle (θ') with respect to the rotation central axis (C) is the largest, but is minimized at the final inclined edge 132 because the angle (θ') with respect to the rotation central axis (C) becomes gradually smaller toward the final inclined edge 132, such that upward advancing speed of the reamer becomes faster so as to enable the user to rapidly carry out hole formation from the initial point to form the hole in the bone 40 to a desired depth.

However, differently from the conventional reamer for implant surgery shown in FIGS. 1 and 2, the reamer according to the present invention does not include the discharge path 140. The conventional reamer includes the discharge path 140 in order to prevent deterioration in rotary power of the cutting part 1 because the discharge path 140 smoothly discharges the residue of the cut bone 40 so as to enhance friction resistance by the residue of the bone 40.

Figure 4:
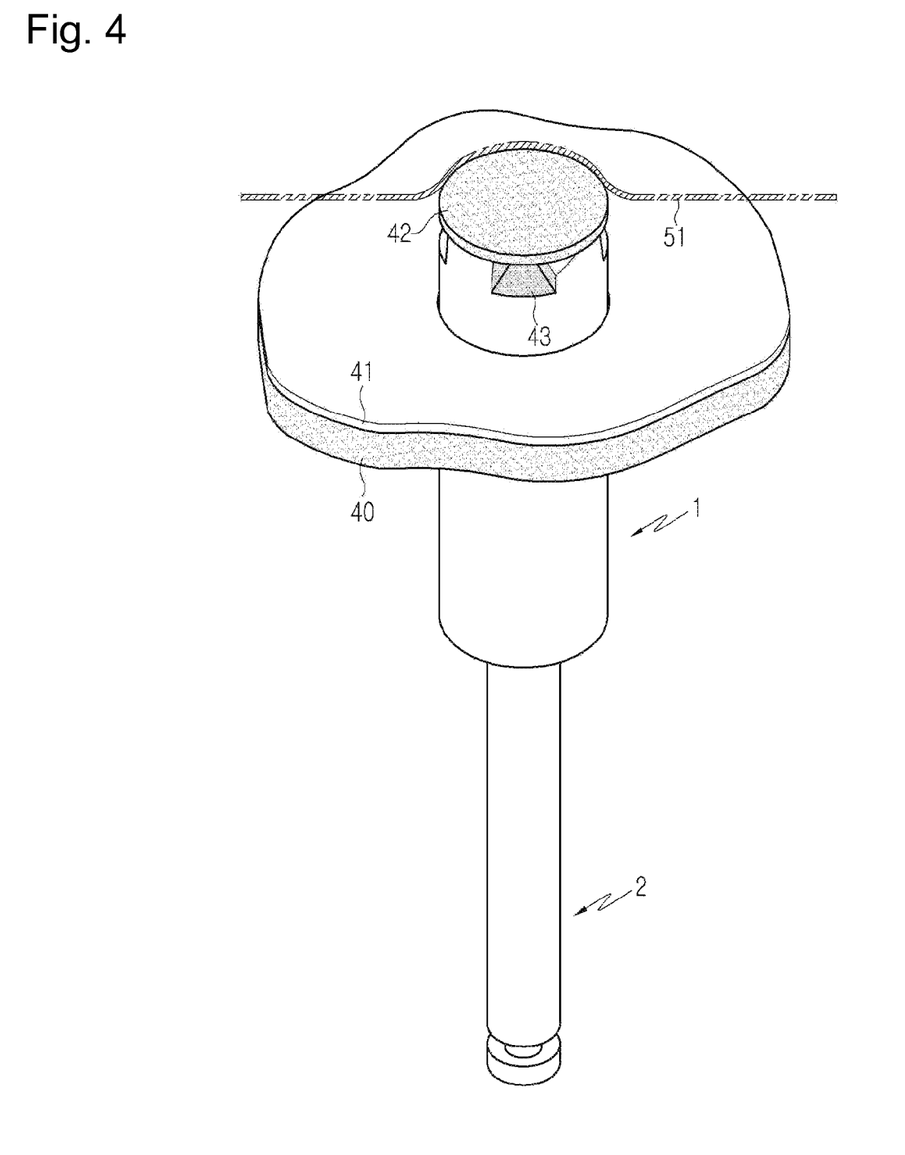
FIG. 4 is a view showing a used state of the reamer for implant surgery according to the preferred embodiment of the present invention.

As shown in the enlarged view of FIG. 3, the reamer includes a bone storage groove 31 formed above the cutting part 1 and formed between the cutting front end portion 10 and the cut edge 20 which are formed radially and alternately with each other. The bone storage groove 31 is to make the residue of the bone 40, namely, the autogenous bone 43, be naturally inserted and accumulated during rotation of the cutting part 1. As shown in FIG. 4, when the cutting part 1 perforates the bone 40 and lifts up the sinus membrane 51 into the maxillary sinus 50, the autogenous bone 43 accumulated in the bone storage groove 31 is inserted into the maxillary sinus 50.

In the meantime, like the convention reamer in which the inclination angles (θ' and θ") between the initial inclined edge 131 and the final inclined edge 132 formed on the side of the conventional reamer are formed to become smaller from the initial inclined edge 131 toward the final inclined edge 132, as shown in the enlarged view of FIG. 3, the reamer according to the preferred embodiment of the present invention the inclination angles of side inclined edges 30 formed on the outer circumferential sides of the cutting front end portion 10 and the cut edge 20 are formed to become smaller in the rotation direction, such that the upward advancing speed of the reamer becomes faster. The side inclined edge 30 according to the preferred embodiment of the present invention is to cut the outer circumferential surface of the hole, and as shown in the enlarged view of FIG. 3, total four side inclined edges 30 are inclinedly formed on the sides of the two cutting front end portions 10 and the two cut edges 20, so that the reamer according to the preferred embodiment of the present invention can enhance cutting power of the outer circumferential surface of the hole and secure and keep a stable centrum.

Figure 5:
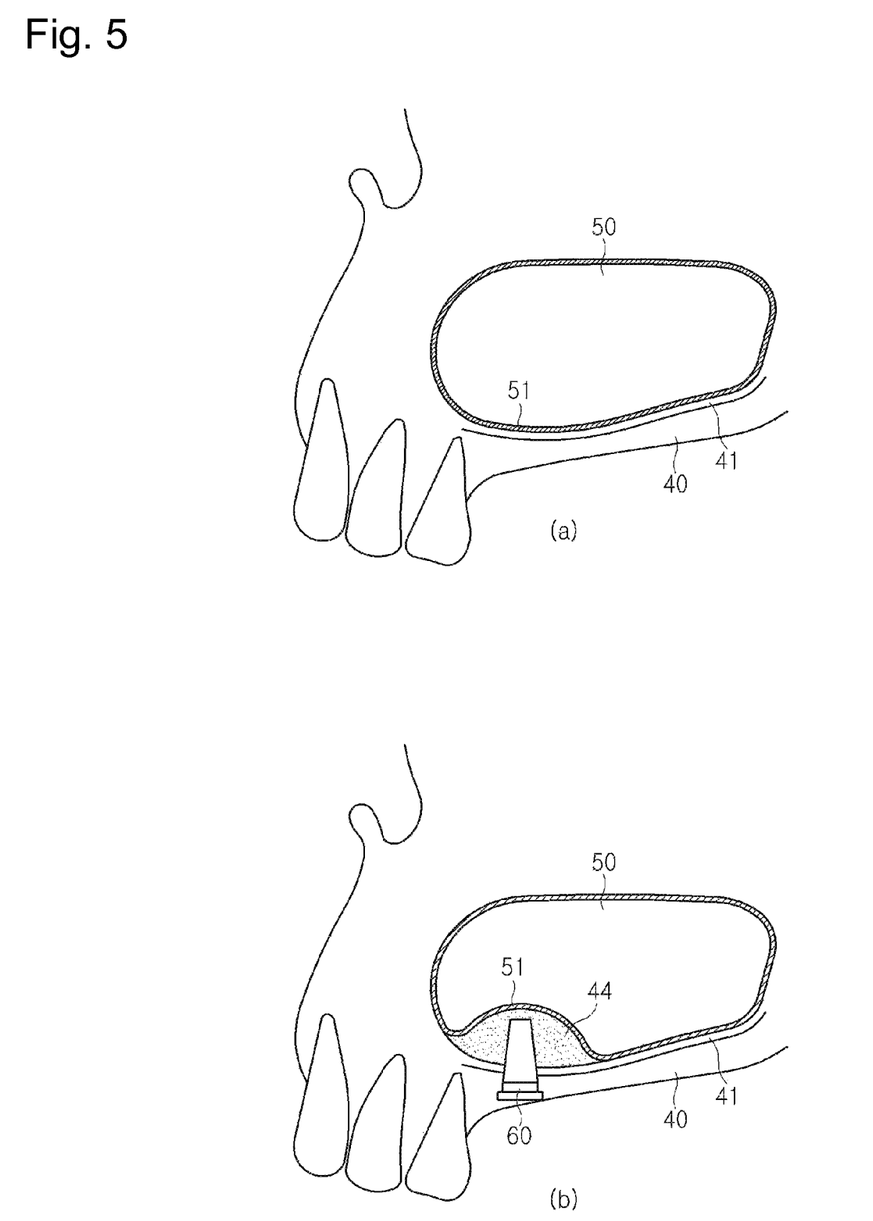
FIG. 5 is an example view for explaining the maxillary sinus and implant operation.

FIG. 4 is a view showing a used state of the reamer for implant surgery according to the preferred embodiment of the present invention, and FIG. 5 is an example view for explaining the maxillary sinus and implant operation. FIG. 5 briefly shows the side of a face obtained by radiography, wherein the bone 40 to which a core 60 of the implant will be planted and the maxillary sinus 50 located above the bone 40 are illustrated, and the maxillary sinus 50 is protected by a sinus membrane 51 of the mucous membrane type.

After the bone 40 is rapidly cut by the cutting front end portions 10 and the cut edges 20, before the upper portion of the cutting part 1 comes into contact with the sinus membrane 51, as shown in FIG. 4, a hard and compact bone 41 is cut into a circular bone fragment 42, and then, the sinus membrane 51 is lifted upwardly to the inside of the maxillary sinus 50 in a state where the upper portion of the cutting part 1 is not in contact with the sinus membrane 51 by means of the bone fragment 42, such that the implant core 60 can be planted into the maxillary sinus 50 as shown in FIG. 5(*b*) without any damage of the sinus membrane 51. After the bone 40 is perforated and the sinus membrane 51 is lifted, the maxillary sinus 50 is filled with the autogenous bone 43 and a transplanted bone 44 in order to firmly fix the implant core 60.

As described above, because the reamer for implant surgery according to the preferred embodiment of the present invention includes: two cutting front end portions 10 having sharp front ends and cut edges 20 of the horizontal line form to get in line contact with the bone 40, which are formed radially and alternately based on the rotation central axis (C) of the cutting part, the reamer can stabilize centrum rotation and enhance cutting efficiency by the cutting front end portions 10 formed symmetrically based on the rotation central axis (C) of the cutting part 1 so as to make high speed rotation possible, thereby increasing cutting power and working speed and keeping a stable cutting position due to the sharp cutting front end portions 10 which are formed symmetrically even when the reamer comes into contact with the bone 40.

Moreover, when the upper portion of the cutting part 1 is rotated in a state where it gets in contact with the bone 40, because the reamer comes into line contact with the bone 40 by the cut edges 20 of the horizontal line form each of which has the inclined face 21 inclined downward toward the rear side, the friction resistance with the bone 40 is reduced, and hence, the reamer according to the preferred embodiment of the present invention can increase cutting power and enhance working speed.

Furthermore, because the reamer includes the bone storage groove 31 formed between the cutting front end portion 10 and the cut edge 20, the residue of the eliminated bone 40 is naturally inserted and accumulated into the bone storage groove 31, such that the residue of the bone 40 does not hinder rotation of the cutting part 1, for instance, increase friction resistance, and the autogenous bone 43 accumulated in the bone storage groove 31 the moment the bone 40 is perforated pushes up the bone plate opened by the structure of the reamer while being inserted into the maxillary sinus 50 so as to prevent a damage of the sinus membrane 51 and to be utilized as a filling material necessary for fixing the implant core 60.

EXPLANATION OF ESSENTIAL REFERENCE NUMERALS IN DRAWINGS

1: cutting part
2: connection part
10: cutting front end portion
11: depressed face
20: cut edge
21: inclined face
22: stepped jaw
30: side inclined edge
31: bone storage groove
40: bone
41: compact bone
42: bone fragment
43: autogenous bone
44: transplanted bone
50: sinus membrane
60: core
110: cutting front end portion
111: depressed face
120: cut edge
121: protruding face
122: stepped jaw
130: tapered portion
131: initial inclined edge
132: final inclined edge
140: discharge path
C: rotation central axis

The invention claimed is:

1. A reamer for implant surgery comprising:
   cutting front end portions (10) which are formed at an upper portion of a cutting part (1) and each of which has a sharp front end;
   cut edges (20) of a horizontal line form, the cutting front end portions (10) and the cut edges (20) being arranged radially and alternately, wherein a rear side of the cutting front end portion (10) having the sharp front end has a triangular depressed face (11) inclined downwardly toward a rotation central axis (C) of the cutting part (1), and a rear side of the cut edge (20) having the horizontal line form has a triangular inclined face (21) inclined downwardly toward an outer circumferential surface of the cutting part (1), wherein storage grooves (31), each of which being configured to receive a residue of a bone (40) being cut is inserted and accumulated, are formed between the cutting front end portions (10) and the rear side of the cut edges (20) and between the cut edges (20) and the rear side of the cutting front end portions (10), which are arranged alternately, and wherein an inclination angle of a side inclined edge (30) formed at sides of the outer circumferences of the cutting front end portion (10) and the cut edge (20) becomes gradually smaller in a rotation direction of the cutting part (1).

\* \* \* \* \*